United States Patent
Mower et al.

(10) Patent No.: US 7,919,114 B2
(45) Date of Patent: *Apr. 5, 2011

(54) **COMPOSITIONS AND METHODS USING *MORINDA CITRIFOLIA***

(75) Inventors: Thomas W. Mower, Elkridge, UT (US); James C. Bawden, Provo, UT (US); Marlin C. Harmon, Bountiful, UT (US); Craig R. Stutz, Orem, UT (US); Chuan Wang, Orem, UT (US)

(73) Assignee: Neways, Inc., Springville, UT (US)

( * ) Notice: Subject to any disclaimer, the term of this patent is extended or adjusted under 35 U.S.C. 154(b) by 1075 days.

This patent is subject to a terminal disclaimer.

(21) Appl. No.: 11/459,322

(22) Filed: Jul. 21, 2006

(65) Prior Publication Data

US 2006/0286188 A1 Dec. 21, 2006

Related U.S. Application Data

(62) Division of application No. 10/612,754, filed on Jul. 1, 2003, now Pat. No. 7,749,535.

(60) Provisional application No. 60/440,131, filed on Jan. 15, 2003.

(51) Int. Cl.
*A61K 9/20* (2006.01)
*A61K 9/48* (2006.01)

(52) U.S. Cl. .................. 424/465; 424/451; 424/464

(58) Field of Classification Search ................ None
See application file for complete search history.

(56) References Cited

U.S. PATENT DOCUMENTS

| | | | |
|---|---|---|---|
| 2,761,783 A | 9/1956 | Ferguson, Jr. | |
| 3,011,897 A | 12/1961 | Grosvenor, Jr. | |
| 4,084,010 A | 4/1978 | Takemoto et al. | |
| 4,408,041 A | 10/1983 | Hirao et al. | |
| 4,690,827 A | 9/1987 | Kupper et al. | |
| 4,717,765 A | 1/1988 | Hirao et al. | |
| 4,725,387 A | 2/1988 | Hirao et al. | |
| 4,758,660 A | 7/1988 | Takeuchi et al. | |
| 4,789,559 A | 12/1988 | Hirao et al. | |
| 4,870,059 A | 9/1989 | Mitsuhashi et al. | |
| 4,917,916 A | 4/1990 | Hirao et al. | |
| 5,225,221 A | 7/1993 | Camden et al. | |
| 5,411,755 A * | 5/1995 | Downton et al. | 426/599 |
| 5,433,961 A | 7/1995 | Lanner et al. | |
| 5,433,965 A * | 7/1995 | Fischer et al. | 426/548 |
| 6,103,240 A | 8/2000 | Zhou | |
| 6,124,442 A | 9/2000 | Zhou et al. | |
| 6,299,925 B1 * | 10/2001 | Xiong et al. | 426/597 |
| 6,387,370 B1 * | 5/2002 | Yegorova | 424/94.2 |
| 6,413,558 B1 | 7/2002 | Weber et al. | |
| 6,416,806 B1 | 7/2002 | Zhou | |
| 6,582,753 B1 | 6/2003 | Willibald-Ettle et al. | |
| 7,014,872 B2 * | 3/2006 | Pushpangadan et al. | 424/725 |
| 2002/0068102 A1 * | 6/2002 | Su et al. | 424/765 |
| 2002/0090406 A1 | 7/2002 | Su et al. | |
| 2002/0132037 A1 | 9/2002 | Zhou | |
| 2005/0085454 A1 | 4/2005 | Ghosal | |

FOREIGN PATENT DOCUMENTS

| | | |
|---|---|---|
| JP | 52-57366 | 5/1977 |
| JP | 52-83986 | 7/1977 |
| JP | 52-143257 | 11/1977 |
| JP | 356117781 A | 9/1981 |
| JP | 56-158072 | 12/1981 |
| JP | 57-86266 | 5/1982 |
| JP | 58-36368 | 3/1983 |
| JP | 58071868 | 4/1983 |
| JP | 358116674 A | 7/1983 |
| JP | 6012074 | 7/1985 |

OTHER PUBLICATIONS

U.S. Appl. No. 10/612,754, filed Jul. 1, 2003, Mower et al.
U.S. Appl. No. 11/173,611, filed Jul. 1, 2005, Mower et al.
Food and Drug Administration, Dept. of Health and Human Services (Title 21—Food and Drugs); Part 101—Food Labeling, (2002).
Food and Drug Administration, Dept. of Health and Human Services (Title 21—Food and Drugs); Part 170—Food Additives, (2002).
Code of Federal Regulations, Title 21, vol. 2, [Revised as of Apr. 1, 2002], Section 101.22, *Foods; labeling of spires, flavorings, colorings and chemical preservatives.* pp. 72-77.
Code of Federal Regulations, Title 21, vol. 3 [Revised as of Apr. 1, 2002], Sec. 170.3, *Definitions.* pp. 5-9.
Office Action dated Jan. 23, 2009 from U.S. Appl. No. 10/612,754, 21 pages.
Office Action dated Jul. 22, 2008 from U.S. Appl. No. 10/612,754, 21 pages.
Office Action dated Jan. 4, 2008 from U.S. Appl. No. 10/612,754, 21 pages.
Office Action dated Apr. 6, 2007 from U.S. Appl. No. 10/612,754, 21 pages.
Office Action dated Oct. 10, 2006 from U.S. Appl. No. 10/612,754, 15 pages.
Office Action dated Aug. 10, 2007 from U.S. Appl. No. 11/173,611, 15 pages.
Office Action dated Jul. 7, 2010 from U.S. Appl. No. 11/173,611.
Office Action dated Sep. 16, 2009 from U.S. Appl. No. 11/173,611.

* cited by examiner

*Primary Examiner* — Humera N Sheikh
(74) *Attorney, Agent, or Firm* — Workman Nydegger

(57) ABSTRACT

Dietary supplements include a complementary blend of fruits including at least noni and Luo Han Guo. Other fruits having a high ORAC value, such as blueberries and raspberries, are also preferably incorporated. The combination of the Luo Han Guo and noni masks the noni's flavors and odors while sweetening the dietary supplements. The Luo Han Guo can be simultaneously provided in both powder and liquid form so that the liquid form acts as the primary sweetener while the powder form acts as the primary masker. The dietary supplements also have an enhanced natural preservative effect, providing an extended shelf life without the use of artificial preservatives.

12 Claims, No Drawings

COMPOSITIONS AND METHODS USING *MORINDA CITRIFOLIA*

CROSS-REFERENCE TO RELATED APPLICATIONS

This application is a divisional of U.S. patent application Ser. No. 10/612,754, filed on Jul. 1, 2003 now U.S. Pat. No. 7,749,535, entitled COMPOSITIONS AND METHODS USING *MORINDA CITRIFOLIA*, which claims the benefit of U.S. Provisional Application No. 60/440,131, filed Jan. 15, 2003.

BACKGROUND OF THE INVENTION

1. The Field of the Invention

The present invention relates generally to dietary supplements incorporating fruit of the *Morinda citrifolia* tree (noni). The invention also relates to, for example, dietary supplements incorporating both fruit of the noni tree and *momordica* fruit and optionally including one or more of raspberries, blueberries, and other fruits having a high oxygen radical adsorption capacity.

2. The Relevant Technology

Historically, native healers have used all parts of the noni tree (*Morinda citrifolia*) medicinally. The fruit, however, is the current focus of most medicinal uses today. For instance, the fruit has been used in Thailand to relieve vomiting and nausea. In Fiji, it has been used to treat ringworm, hemorrhoids, and oral problems such as bad breath, hoarseness, and mouth ulcers. In the Cook Islands, noni juice has been used to treat urinary tract infections and abdominal swellings. The plant is also found throughout India where the fruit is claimed to be a laxative and emmenagogue. Some Hawaiian healers have gone so far as to tout noni's anti-cancer effects. As a result of these widespread uses and reported benefits, there has arisen a large demand for noni juice as a dietary supplement.

Noni fruit contains trace amounts of over 160 chemical substances, the most important of which are its unique polysaccharides. These unique heteropolysaccharides are composed mainly of the sugars glucuronic acid, galactose, arabinose, and rhamnose. Various studies have found that a combination of these noni polysaccharides have a significant beneficial effect.

Despite the well-known benefits of consuming noni juice, there are several aspects of noni juice that limits its widespread use and acceptance. For example, noni degrades quickly. When a noni fruit falls off a tree, for example, it will develop mold and rot within two to three hours. By way of comparison, similar mold and rot may take days to develop on an apple that falls from a tree. This problem of quick degradation exists not only with noni fruit, but with noni fruit juices and noni-based dietary supplements as well.

The best method to preserve the valuable noni polysaccharides for human use has been an area of debate, trial and error, and scientific breakthroughs. Fermentation (using decayed fruit) of noni is a relatively new method of production, one not used by traditional healers. Fermentation is an easy method of production that also makes the taste and smell of noni less noxious. However, the fermentation industry has developed into a sloppy production method preferred by commercial producers but less favored by traditional healers, and hence the typical consumers of dietary supplements.

Another aspect of the noni fruit that can serve as a barrier to it use is its noxious smell and taste. As a result, conventional noni-based dietary supplements typically have less than 5 percent noni. In response to this problem, numerous approaches have been made to overcome noni's noxious smell and taste, including artificial sweeteners and the use of other fruit juices such as grape juice. Nevertheless, artificial sweeteners may have negative health consequences and are therefore widely disfavored among the typical users of dietary supplements. Further, the use of natural fruit juices has thus far proven to be of limited success in overcoming the noxious smell and taste of noni fruit juice.

In view of the foregoing, there is a continuing need for improved methods of producing dietary supplements incorporating noni fruit as well as methods and compositions for providing more palatable dietary supplements incorporating noni fruit.

SUMMARY OF THE INVENTION

The herein disclosed dietary supplements comprise a complementary blend of noni (*Morinda citrifolia*) and Luo Han Guo (*Momordica*) and optionally one or more of blueberries, raspberries, and other fruits having a high ORAC (Oxygen Radical Absorption Capacity) value. The fruits are preferably provided as fruit juices, such as in frozen puree concentrate form, although other forms may be compatible. The combination of health benefits provided by these fruits synergistically supports the body's natural defense mechanisms and helps maintain good health. The juices maintain cellular health at various levels and by various mechanisms.

The dietary supplements may comprise noni and Luo Han Guo with or without one or more of the ingredients disclosed herein or otherwise known in the art. For example, the dietary supplements can comprise noni, Luo Han Guo, blueberry, and raspberry. The Luo Han Guo can be simultaneously provided in both powder and liquid form. In this embodiment the Lo Han Guo acts as the primary sweetener while the powder Lo Han Guo acts as the primary masker of noni's unpleasant taste and odors. According to one embodiment of the invention the liquid and powder Lo Han Guo are used to mask an unpleasant taste of, and sweeten, a dietary supplement other than noni.

The herein disclosed dietary supplements also have an enhanced natural preservative effect, allowing an extended shelf life without the use of artificial preservatives.

These and other features of the present invention will become more fully apparent from the following description and appended claims, or may be learned by the practice of the invention as set forth hereinafter.

DETAILED DESCRIPTION OF THE INVENTION

I. Introduction

The herein disclosed dietary supplements comprise a complementary blend of noni (*Morinda citrifolia*) and Luo Han Guo (*momordica*) and optionally one or more of blueberries, raspberries, and other fruits having a high ORAC (Oxygen Radical Absorption Capacity) value. The fruits are preferably provided as fruit juices, such as in frozen puree concentrate form, although other forms may be compatible. The combination of health benefits provided by these fruits synergistically supports the body's natural defense mechanisms and helps maintain good health. The juices maintain cellular health at various levels and by various mechanisms.

The dietary supplements may comprise noni and Luo Han Guo with or without one or more of the ingredients disclosed herein or otherwise known in the art. For example, the dietary supplements can comprise noni, Luo Han Guo, blueberry, and raspberry. The particular additional ingredients selected will depend upon the desired design characteristics of a particular product. Important design considerations include, for example: flavor, smell, polysaccharide levels, pH, color, stability, nutritional value, medicinal benefits, and synergistic effects. According to one embodiment of the invention the liquid and powder Lo Han Guo are used to mask the unpleasant taste of, and sweeten, a dietary supplement other than noni.

Dietary supplements formulated as disclosed herein have the added advantage of a surprisingly pleasant taste, despite the presence of the noni, which is known to have a noxious taste and odor. The dietary supplement's smooth, rich, natural flavor results from the naturally sweet fruit extracts despite the lack of added sugars or artificial sweeteners, although they may be used in some embodiments. The flavor is also benefited by the lack of added preservatives.

Additionally, it has been surprisingly discovered that the herein disclosed dietary supplements display a surprising preservative effect. In challenge testing wherein bacteria was introduced to a dietary supplement, the dietary supplement actually eliminated the bacteria, thus evidencing a striking ability of the dietary supplement to withstand degradation and maintain a longer shelf life. Although the present invention is not limited by the following theory that may in part explain the preservative effect of the dietary supplements, it is presently believed that the symbiotic effects of the *momordica* with the strong antioxidants in blueberries and raspberries provide the preservative effect that extends the shelf life of the dietary supplements.

Additional advantages of the present invention will become readily apparent to those skilled in the art from the following detailed description, wherein currently preferred embodiments of the invention are shown and described in the disclosure. As will be realized, the invention is capable of other and different embodiments, and its several details are capable of modifications in various obvious respects, all without departing from the invention. Accordingly, the description is to be regarded as illustrative in nature, and not as restrictive.

In the following description, numerous specific details are set forth in order to provide a thorough understanding of the present invention. It will be obvious, however, to one skilled in the art that the present invention may be practiced without these specific details. In other instances, well known aspects of dietary supplements have not been described in particular detail in order to avoid unnecessarily obscuring the present invention. Concentrations of each of the components of the dietary supplements are presented in their preferred form which typically includes a certain percentage of water. One skilled in the art will recognize that it is a simple matter to account for the water in determining the effective amount of the fruit that is present in a recited concentrate.

II. Compositions

A. Noni

The origin of the noni tree (*Morinda citrifolia*) is ubiquitous, but now appears to have its phylogenetic start in New Calcdonia. However, some good data show that it is likely to have originated in Southeast Asia. Regardless of origin, noni trees rapidly became part of the normal flora across the islands of the South Pacific. Historically, native island healers use all portions of the plant medicinally. The noni fruit (hereinafter "noni") is the current focus of most cultures today as it has been used for many years to treat a wide variety of illnesses. For instance, the fruit has been used in Thailand to relieve vomiting and nausea. In Fiji, it has been used to treat ringworm, hemorrhoids, and oral problems such as bad breath, hoarseness, and mouth ulcers. In the Cook Islands, noni juice has been used to treat urinary tract infections and abdominal swellings. The plant is also found throughout India where the fruit is claimed to be a laxative and emmenagogue. The most interesting claims originated in Hawaii, where Hawaiian healers tout noni's anti-cancer effects.

Noni fruit contains trace amounts of over 160 chemical substances, the most important of which are its unique polysaccharides. These unique heteropolysaccharides are composed mainly of the sugars glucuronic acid, galactose, arabinose, and rhamnose. Studies with animals have found that a combination of these noni polysaccharides with chemotherapy has a significant beneficial effect by allowing the use of sub-optimal doses of chemotherapy while nevertheless improving the curative property.

Early studies indicated that noni polysaccharides indirectly enhanced the host immune system, especially macrophages and lymphocytes. It was later shown that macrophage production was stimulated in a bi-phasic and synergistic up-cycling of these important immune cells. For example, one specific irridoid chemical found in noni has direct anti-clastogenic and anti-mutagenic activities. More recently, a variety of mechanisms have been demonstrated for tumor cell suppression: 1) noni inhibits DNA adduct formation in rodents via inhibition of phase I enzyme activity and simultaneous enhancement of phase II enzyme activity leading to DNA repair mechanisms; 2) noni releases several immune modulators including tissue necrosis factor alpha-3, several interleukins, and nitric oxide II; 3) noni inhibits the "ras" gene leading to slowed tumor growth; 4) noni suppresses TPA and EGF-induced cell transformation and associated AP-1 activity which slows tumor growth; and 5) noni has been shown to be a better antioxidant than vitamin C, pycnogenol, or grape seed extract. A detailed report on antioxidant activity is presented in the blueberry section herein. Additionally, similar polysaccharides derived from fungal species (certain mushrooms) also show significant anti-tumor effects.

The best method to preserve these polysaccharides for human use has been an area of debate, trial and error, and scientific breakthroughs. Fermentation (using decayed fruit) of noni is a relatively new method of production, one not used by traditional healers. Fermentation is an easy method of production that also makes the taste and smell of noni less noxious. However, the fermentation industry has developed into a sloppy production method preferred by commercial producers but disfavored by traditional healers, and hence most conventional consumers of dietary supplements.

Likewise, dried or "chipped" fruit has been shown to cause extreme instability of the noni fruit, with degradation of products and microbial contamination. Ripe fruit becomes putrid within 3 to 5 days. Thus, the only way to commercially capture and retain fresh noni is to puree and flash-pasteurize the fruit, which retains high levels of polysaccharides in the puree. The other safe method of preservation is freeze-drying the fruit, although this is expensive and has not shown superior results. The only continuously reproducible method with proven results is puree.

Another preferred form is a highly refined puree known as micronized puree. Other compatible, albeit less preferred, noni forms include fermented paste, fermented juice, dry powder, freeze dried, and oven blasted.

Noni puree is preferably included as a 3:1 noni:water concentrate in a range by weight of the dietary supplement from about 5 to about 25 percent, more preferable from about 5 to about 20 percent, still more preferably from about 5 to about 15 percent, and still more preferably from about 8 to about 13 percent. Of course, equivalent amounts of noni can be supplied through other forms as mentioned hereinabove.

B. Luo Han Guo

The varieties of fruit known as Luo Han Guo come from the family Cucurbitaceae, tribe Jollifieae, subtribe Thladianthinae, genus *Siraitia* and include the genus/species *S. grosvenorii, S. siamensis, S. silomaradjae, S. sikkimensis, S. africana, S. borneensis*, and *S. taiwaniana*. The Chinese plant *S. grosvenorii*, or *Momordica grosvenorii*, is referred to as Luo Han Guo in most Chinese Provinces, called Rakanka in Japan, and also known as Chinese Bitter Melon. Other common names for *S. grosvenorii* include Lo Han Kuo, Arhat Fruit, and Fructus Momordicae. Although the fruits and leaves of the principal cultivated varieties have been described as showing striking differences in shape and color of the fruit and leaves, they are generally included together in China. Therefore, the fruit of the above plant varieties will be herein collectively referred to as "Luo Han Guo." For a further description of Luo Han Guo, its related plant varieties, and its uses as a sweetener, see U.S. Pat. No. 5,433,965 to Fischer et al, herein incorporated by reference.

Traditionally, Luo Han Guo fruits are dried and stored in the dry state until used. The dried fruits are used whole, as extracts, or in powdered or block forms. The powdered fruit form is often preferred because it is less expensive because it is less prone to problems with microbial growth, does not require refrigeration, is easier transport, and has a longer shelf life.

The prepared block form "Luohanguo Chongji" is a popular treatment for colds and the dried fruits are used in a variety of traditional Chinese medicines, such as analgesics, expectorants, antitussives, and treatments for the infiltration of the lungs.

While the drying process preserves the fruit and removes most of the objectionable flavor from the fresh fruit, it also causes the formation of bitter, astringent and brown flavors. These flavors restrict the use of the dried fruits and dried fruit extracts to the preparation of dilute teas and soups and products to which sugar, honey and the like are added.

More recently, the "sweet principles" of Luo Han Guo are of great interest to diabetics, to people watching their calorie intake, and in dental health. This is due in large part to the triterpene glycosides which act as non-caloric sweeteners in Luo Han Guo, also known as mogrosides. Recent reports are of particular interest because they show that mogrosides prevent LDL oxidation (a potential therapy for atherogenic disease) and are anti-cariogenic to teeth. A dental laboratory study clearly demonstrated two mechanisms of action against tooth decay. Firstly, Luo Han Guo does not provide a growth medium for *Streptococcus mutans* (the most common dental pathogen), like simple sugars (sucrose, glucose, and fructose). Secondly, Luo Han Guo physically impairs *S. mutans* from adhering to hard surfaces.

Liquid extracts of Lo Han Guo can be as much as 300 times sweeter than sucrose, depending on the extraction method. In addition, Lo Han's antioxidant effects may provide antioxidant synergism with other antioxidants in the herein disclosed dietary supplements.

According to one embodiment of the invention, it has been surprisingly discovered that Luo Han Guo can be added in two different potencies in order to maximize its effect while minimizing the amount required, and hence its cost. A powdered low concentration form is used to mask the flavor and scent of the noni and provide a very rich, deep flavor. A higher concentration liquid form is added as a sweetener. Of course, a lower amount of one in the dietary supplement would require a higher amount of the other, and vice versa. The use of this combination of Luo Han Guo forms is effective because typically the powder form has been only extracted once, and therefore maintains it rich, deep flavor. It is this rich taste that is often called bitter and has earned the fruit the name "Chinese bitter melon." In contrast, the liquid form of the fruit is typically extracted repeatedly, thereby removing the rich taste of the fruit and leaving a sweet taste. Hence, the powder Luo Han Guo masks the undesirable flavor of the noni while the liquid Luo Han Guo sweetens the dietary supplement. Of course, each of the liquid and powder forms can be obtained that have been either extracted once or more than once, in which case various combinations of once extracted and multiple-times extracted *momordica* in either or both liquid and powder forms can be used.

The liquid Luo Han Guo is preferably supplied in a 7:1 or 8:1 Luo Han Guo:water ratio based upon current supplier preferences. The powder Luo Han Guo is preferably supplied as 5 percent Luo Han Guo, with the rest comprising a filler. The amount of *momordica* that is used in the dietary supplements will vary depending on the concentration of the noni and other ingredients in the dietary supplement, but will comprise at least an effective amount to sweeten the dietary supplement and/or mask the taste of the noni. Preferred amounts comprise 0.1 percent to 1 percent by weight of the dietary supplement of the liquid *momordica* and 0.1 percent to 2 percent by weight of the dietary supplement of the powder *momordica*.

C. Other Fruits

In addition to noni and Luo Han Guo, a variety of other fruits can be advantageously incorporated in the herein disclosed dietary supplements. A number of factors can be used in selecting appropriate fruits, including, for example, flavor, smell, color, nutritional value, and medicinal benefits. Optimally, however, such additive fruits will have a high ORAC (Oxygen Radical Absorption Capacity) value, which measures their antioxidant capacity. Typically, fruits with an ORAC value of greater than 1000 ORAC Units per 100 gm of fruit are considered to have a high ORAC value. Such fruits are particularly healthful and commercially desired because of these high antioxidant effects. Of course, other high ORAC value foods, such as high ORAC value vegetables, can also be included. These include, again by way of example, kale, spinach, Brussels sprouts, alfalfa sprouts, broccoli florets, beets, and red bell peppers, and other high ORAC value vegetables that are well known in the art.

Additionally, there is some data known in the art showing that effective antioxidant protection requires the ingestion of a variety of antioxidant entities. It is theorized that this is because the combination of the different antioxidant entities leads to synergistic effects that provide the greatest health benefits. Thus, according to one preferred aspect of the invention, several high ORAC value fruits are incorporated in the dietary supplements.

The most preferred fruits are raspberry and blueberry, which are effective antioxidants and thereby provide increased cellular health. Other preferred fruit concentrates having a high ORAC value include, by way of example only, grapes, blackberries, strawberries, plums, oranges, cherries, and kiwi fruits, currants, elderberries, black currants, cranberries, and others that are well known in the art. Various of the fruit juices that are acceptable for use in the dietary supplements of the present invention, such as raspberry and blueberry, are commercially available from the natural juice company Ocean Spray, located in Prosser, Wash.

1. Blueberry

Blueberry extracts are potent antioxidants due largely in part to the flavonoids found therein. Generally, over 4,000 different flavonoids have been identified, of which approximately 150 have been extensively studied. It is known that blueberries contain high concentrations of one subclass of flavonoids, the darkly colored anthocyanins. One anthocyanin, theaflavin, gives blueberries their deep blue color. Blueberry anthocyanins now appear to be the most powerful antioxidants among flavonoids. In addition to their antioxidant properties, anthocyanins are also able to neutralize certain destructive enzymes such as metalloproteinases, initiate anti-inflammatory effects on blood vessels, inhibit serum protein decreases induced by hyperoxia, assist the body in dissolving blood clots, and exhibit anticancer effects not directly related to reactive oxygen species (ROS).

ROS leads to chronic human diseases. Antioxidant interference with oxidization of low-density lipoproteins (LDL) has been firmly established as a major retardant of cardiovascular disease (CVD). For example, one study suggested that anthocyanins are the key component in red wine that protects against cardiovascular disease rather than the commonly theorized active constituent, resveratrol.

In the last few years, many other chronic diseases have been linked to free-radical induced cellular damage. Additionally, it has been shown that fruit antioxidants can reverse some age-related neuronal/behavioral dysfunctions in animal models, increase dexterity and other motor skills, and increase cognition. Anthocyanins found in fruits and vegetables are as effective in the normalization of neuronal aging and behavior as they are in the prevention of carcinogenesis and CVD.

More recent studies have shown that blueberry anthocyanins are more bioavailable than most other antioxidants. Many antioxidants do not reach therapeutic levels in plasma or tissues because they cannot penetrate and cross cell membranes. However, anthocyanins penetrate physiologic barriers, including the central nervous system, more effectively than other antioxidants. Anthocyanins linger in the body and are not rapidly metabolized, thus leading to longer lasting therapeutic effects.

Other conditions where anthocyanins have shown promising results are: 1) stroke; 2) capillary damage due to diabetic vascular disease; 3) hypertensive vessel damage; 4) arthritic or muscle conditions involving damaged collagen and/or elastin; 5) other inflammatory conditions associated with prostaglandins; 6) immune cell function; and 7) treatment of urinary tract infections. More inclusively, oxidative damage can be observed within every class of bio-molecule, including nucleic acids, proteins, lipids, and carbohydrates. Although much of the possible oxidative damage is not directly attributable to a primary mechanism (as seen in over-eating or intense exercise), it is often secondary to excessive oxidative stress resulting from beta-amyloid-induced free radicals, mitochondrial abnormalities, inadequate energy supply, inflammation, or altered antioxidant defenses.

Blueberries also contain ellagic acid, a substance reported to have anti-cancer properties.

The blueberries are preferably supplied as a concentrate in a 7:1 or 8:1 blueberry:water ratio based upon current supplier preferences. Blueberry fruit concentrate is preferably included in the dietary supplements according to the invention in a range from about 0 percent to about 6 percent, more preferably from about 1 percent to about 3 percent. Of course, equivalent amounts of blueberries can be supplied in other forms, such as juice, powder, freeze dried, etc.

2. Raspberry

Raspberries have a wide variety of flavonoids and an extremely high concentration of the natural anti-mutagen ellagic acid. Ellagic acid offers unique health benefits unrelated to its antioxidant potential. In addition, since raspberries contain unique anthocyanin flavonoids (ellagitannins, kaempferol, procyanidin, and quercetin, it is an ideal part of a multicomponent antioxidant system. Recently, researchers found that procyanidins block cell cycle at the G2/M phase, thereby providing anti-tumor activity. The same research also noted that procyanidins block key enzymes in polyamine synthesis, thus slowing tumor growth. Others have concluded that raspberries in orally available doses have the ability to prevent cataract formation. These researchers theorized that the mechanism of eye protection was due to a unique antioxidant effect.

More than 125 studies done with Ellagic acid have demonstrated the efficacy of this natural food acid. The following is a brief compilation of effects seen with raspberry and/or ellagic acid documented in these studies: 1) an ability of ellagic acid to modulate gene expression in prostate cancer cell cultures; 2) inhibition of liver cancer cells by multiple mechanisms; 3) inhibition of multiple enzyme systems that promote bladder cancer cell growth; 4) protection of the colon mucosa leading to prevention of pre-cancerous cell formation; 5) inhibition of chemically induced esophageal cancer; 6) inhibition of chemically-induced lung tumors; 7) activity against leukemic cells in vitro; and 8) inhibition of chemically-induced skin carcinoma in mice.

A wide variety of mechanisms for the anti-tumorigenic effects of ellagic acid have been proposed. Some of these mechanisms are: 1) enzyme inhibition; 2) effects on DNA adduct formation; 3) a role in G1 arrest and apoptosis; 4) protective modulation of DNA even in cases where other antioxidants appear to increase DNA damage; and 5) protection against gamma-radiation (hydroxyl radicals).

Other unique cellular effects of ellagic acid and/or raspberry are: 1) protection of the stomach mucosal lining through multiple mechanisms; 2) protection of the colon lining against colitis type invasions which may produce pre-cancerous cells; and 3) an anti-bacterial effect that could be used as a functional preservative.

The raspberries are preferably supplied as a frozen concentrate a 7:1 or 8:1 raspberry:water ratio based upon current supplier preferences. Raspberry fruit concentrate is preferably included in the dietary supplements according to the invention in a range from about 0 percent to about 6 percent, more preferably from about 1 percent to about 3 percent. It has been determined according to the invention that the combination of raspberry and blueberry fruit concentrates is particularly advantageous. In this case it is preferred to include from about 1 percent to about 3 percent of each of raspberry and blueberry fruit concentrates. As with the other ingredients, raspberries can be supplied in other known forms.

D. Other Ingredients

Preferably, the herein disclosed dietary supplements will include one or more additional well known components of juices, including, for example, sodium chloride and a thickener such as xanthan gum or Konjac-a (glucomanna). Each of these is preferably included in a range from about 0.1 to 1 by weight of the dietary supplement.

Although the herein disclosed dietary supplements have the advantage of being preservative free, it is of course contemplated that there may arise circumstances such as marketing or regulatory situations where the use of preservatives is desired or even required. Accordingly, both natural and artificial preservatives may be used with the embodiments of the invention, including for example, potassium sorbate, sodium benzoate, methylparaben, natamax, and other preservatives that are known in the art or will be made known or developed hereafter.

Similarly, although not required, both additional natural and artificial flavoring ingredients may also be used.

Examples of such flavoring ingredients include lemon juice flavoring, stevia, agave nectar, sucralose, corn syrup, and other sweeteners or flavorings that are known in the art or will be made known or developed hereafter. Lemon juice is particularly preferred and is preferably included in a range from about 0.1 percent to about 1 percent by weight of the dietary supplements.

In addition, the herein disclosed supplements will preferably have a pH value that is preferred for fruit juices. Thus, citric acid, for example, may be added included in a range from about 0.1 percent to about 1 percent by weight of the dietary supplements to set the pH at a level from about 3 to about 4.

Other potential ingredients include stabilizers such as maltodextrin and colorants such as beet juice.

Of course, the largest single ingredient in juice based dietary supplements is water. The quantity of water in the present dietary supplements is calculated to be the amount necessary to reconstitute the fruit concentrates and provide the desired dilution for the dietary supplements.

III. Methods of Preparing

Preferably, after the noni fruit is harvested, it is processed according to various aseptic techniques to provide a sterile refrigerated puree concentrate. Similarly, other fruit concentrates used in the dietary supplements, such as the blueberry and raspberry, are preferably obtained as refrigerated concentrates. The ingredients are then mixed under aseptic conditions and flash pasteurized to minimize microbes and maintain the flavor. The dietary supplement mixture is then bottled in an aseptic environment. This aseptic processing system, in conjunction with the natural preservative effects of the various ingredients, provides a shelf life of at least one year. After opening, refrigeration is sufficient to maintain the dietary supplement for an additional 30 days. Thus, although preservatives may be added to further extend the shelf life, they are not necessary. The aforementioned process also preserves the natural flavors of the juices so that no artificial sweeteners are necessary. Thus, the above process provides a fresh, fruity taste for the dietary supplements and maintains the activity of the juice's enzymes.

In contrast, conventional fruit-based dietary supplements are processed by boiling various ingredients and then bottling. This process reduces or eliminates the activity of many of the juice's enzymes and reduces the juice's natural flavors.

The following examples are given to illustrate the present invention, and are not intended to limit the scope of the invention.

EXAMPLES

In the following examples, the noni is provided in concentrated form in a 3:1 noni:water ratio and the raspberry extract, blueberry extract, and liquid Luo Han Guo are provided in concentrated form in an approximately 7:1 or 8:1 fruit concentrate:water ratio. The powder Luo Han Guo is approximately 5 percent Luo Han Guo.

A dietary supplement formulation was prepared as presented in the following Example 1:

Example 1

| COMPONENT | PER LITER | WT % |
| --- | --- | --- |
| Noni Puree Concentrate | 100 g | 9.7 |
| Raspberry Fruit Concentrate | 18 g | 1.8 |
| Blueberry Fruit Concentrate | 14 g | 1.4 |
| Luo Han Guo Fruit Concentrate: Liquid | 1.7 g | 0.17 |
| Luo Han Guo Fruit: Powder | 7.5 g | 0.75 |
| Natural Lemon Flavor | 2.5 g | 0.25 |
| Xanthan Gum | 2.8 g | 0.28 |
| Sodium Chloride | 1.5 g | 0.15 |
| Citric Acid | 1 g | 0.1 |
| Water | Fill | Fill |
| Total | 1000 g | 100.00 |

Dietary supplements as prepared in Example 1 above (as well as in Examples 2-6) are preferable administered as about two tablespoonfuls (30 ml) orally each morning on an empty stomach.

Additional dietary supplement formulations are prepared as presented in the following Examples 2-6. In each, dietary supplements are prepared with the following weight percents of each of the following components. Water is then added to obtain the desired reconstitution of the concentrates and to obtain the desired product dilution.

Example 2

| COMPONENT | PER 1000 g | WT % |
| --- | --- | --- |
| Noni Puree Concentrate | 97.5 g | 9.75 |
| Raspberry Fruit Concentrate | 18.5 g | 1.85 |
| Blueberry Fruit Concentrate | 14.5 g | 1.45 |
| Luo Han Guo Extract (80% Mogrosides) | 1.2 g | 0.12 |
| Natural Lemon Flavor | 1.3 g | 0.13 |
| Xanthan Gum | 1.3 g | 0.13 |
| Sodium Chloride | 1.2 g | 0.12 |
| Citric Acid | 1.2 g | 0.12 |
| Water | 863.3 g | Fill |
| Total | 1000 g | 100.00 |

Example 3

| COMPONENT | LOW WT % | HIGH WT % |
| --- | --- | --- |
| Noni Puree Concentrate | 5 | 25 |
| Raspberry Fruit Concentrate | 1 | 3 |
| Blueberry Fruit Concentrate | 1 | 3 |
| Luo Han Guo Fruit Concentrate: Liquid | 0.1 | 1 |
| Luo Han Guo Fruit: Powder | 0.5 | 2 |
| Natural lemon flavor | 0.1 | 1 |
| Xanthan Gum | 0.1 | 1 |
| Sodium chloride | 0.1 | 1 |
| Citric Acid | 0.1 | 1 |
| Water | Fill | Fill |
| Total | 100.00 | 100.00 |

Example 4

| COMPONENT | LOW WT % | HIGH WT % |
|---|---|---|
| Noni Puree Concentrate | 8 | 13 |
| Raspberry Fruit Concentrate | 1 | 3 |
| Blueberry Fruit Concentrate | 1 | 3 |
| Luo Han Guo Fruit Concentrate: Liquid | 0.1 | 1 |
| Luo Han Guo Fruit: Powder | 0.1 | 2 |
| Natural lemon flavor | 0.1 | 1 |
| Xanthan Gum | 0.1 | 1 |
| Sodium chloride | 0.1 | 1 |
| Citric Acid | 0.1 | 1 |
| Water | Fill | Fill |
| Total | 100.00 | 100.00 |

Example 5

| COMPONENT | LOW WT % | HIGH WT % |
|---|---|---|
| Noni Puree Concentrate | 5 | 20 |
| Fruit Concentrate | 0 | 6 |
| Luo Han Guo Fruit Concentrate: Liquid | 0 | 1 |
| Luo Han Guo Fruit: Powder | 0 | 2 |
| Natural lemon flavor | 0 | 1 |
| Xanthan Gum | 0 | 1 |
| Sodium chloride | 0 | 1 |
| Citric Acid | 0 | 1 |
| Water | Fill | Fill |
| Total | 100.00 | 100.00 |

According to Example 5, the liquid and powder Luo Han Guo will collectively have a weight percent of at least 0.1.

Example 6

| COMPONENT | LOW WT % | HIGH WT % |
|---|---|---|
| Noni Puree Concentrate | 8 | 13 |
| High ORAC Value Fruit Concentrate(s) | 0 | 6 |
| Luo Han Guo Fruit Concentrate | 0.015 | 3 |
| Natural lemon flavor | 0 | 1 |
| Xanthan Gum | 0 | 1 |
| Sodium chloride | 0 | 1 |
| Citric Acid | 0 | 1 |

Example 7

A dietary supplement was prepared according to the composition of Example 1. The dietary supplement was then challenge tested in accordance with standard procedures by applying a sample of microbes, including yeasts (*Candida albicans, Aspergillus niger*) and several bacteria (*Staphylococcus aureus, Pseudomonas aeruginosa, Escherichia coli,* and *Salmonella typhi*). As evidenced in the following table, it was determined that the dietary supplement actually reduced the bacteria population rather than permit growth, which had been expected.

| ORGANISM | INITIAL | 48 HOURS | ONE WEEK | ACCELERATED TESTING (3 months at 47° C.) |
|---|---|---|---|---|
| *Staphylococcus aureus* | >1000 cfu/ml | <1000 cfu/ml | Sterile | Sterile |
| *Pseudomonas aeruginosa* | >1000 cfu/ml | <1000 cfu/ml | Sterile | Sterile |
| *Escherichia coli* | >1000 cfu/ml | <1000 cfu/ml | Sterile | Sterile |
| *Salmonella typhi* | >1000 cfu/ml | <1000 cfu/ml | Sterile | Sterile |
| *Candida albicans* | >1000 cfu/ml | <1000 cfu/ml | Sterile | Sterile |
| *Aspergillus niger* | >1000 cfu/ml | <1000 cfu/ml | Sterile | Sterile |

Subsequent testing showed approximately the same with the exception of *Staphylococcus aureus* being resistant to the antibacterial effects of the product. This is a very familiar scenario because Staph mutates and becomes resistant to all known antibiotics over time.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A dietary supplement comprising:
   noni puree concentrate comprising at least about 5 percent by weight of the dietary supplement;
   liquid Luo Han Guo fruit concentrate comprising at least about 0.1 percent by weight percent of the dietary supplement so as to sweeten the dietary supplement;
   powder Luo Han Guo comprising at least about 0.1 percent by weight percent of the dietary supplement to mask flavor and/or scent of the noni fruit;
   at least one of a raspberry product or a blueberry product added in an amount of at least about 1 percent by weight of the dietary supplement;
   water; and
   optionally including one or more natural or artificial flavoring ingredients, sodium chloride, one or more thickening ingredients, and citric acid.

2. The dietary supplement of claim 1, wherein:
   the noni puree concentrate comprises from about 5 percent to about 25 percent by weight of the dietary supplement;
   the liquid Luo Han Guo fruit concentrate comprises from about 0.1 percent to about 1 percent by weight percent of the dietary supplement; and the powder Luo Han Guo fruit concentrate comprises from about 0.1 percent to about 2 percent by weight percent of the dietary supplement.

3. The dietary supplement of claim 2, wherein the noni puree concentrate comprises from about 8 percent to about 13 percent by weight of the dietary supplement.

4. The dietary supplement of claim 1, further comprising:
raspberry fruit concentrate from about 1 percent to about 3 percent by weight of the dietary supplement; and
blueberry fruit concentrate from about 1 percent to about 3 percent by weight of the dietary supplement.

5. The dietary supplement of claim 1, further comprising one or more fruits selected from the group consisting of raspberries, blueberries, grapes, blackberries, strawberries, plums, oranges, cherries, and kiwi fruits, currants, elderberries, black currants, and cranberries.

6. A dietary supplement comprising:
noni puree concentrate comprising from about 5 percent to about 20 percent by weight of the dietary supplement;
liquid Luo Han Guo fruit concentrate comprising from about 0.1 percent to about 1 percent by weight percent of the dietary supplement, wherein the liquid Luo Han Guo fruit concentrate sweetens the dietary supplement;
powder Luo Han Guo comprising from about 0.1 percent to about 2 percent by weight percent of the dietary supplement, wherein the powder Luo Han Guo masks the flavors and odors of the noni;
raspberry fruit concentrate from about 1 percent to about 3 percent by weight of the dietary supplement;
blueberry fruit concentrate from about 1 percent to about 3 percent by weight of the dietary supplement;
water; and
optionally including one or more natural or artificial flavoring ingredients, sodium chloride, one or more thickening ingredients, and citric acid.

7. The dietary supplement of claim 6, wherein the noni puree concentrate comprises from about 8 percent to about 13 percent by weight of the dietary supplement.

8. The dietary supplement of claim 6, wherein the powder Luo Han Guo powder was extracted only once from a Luo Han Guo fruit source and wherein the liquid Luo Han Guo was extracted more than once from a Luo Han Guo fruit source.

9. The dietary supplement of claim 6, further comprising a fruit concentrate having an ORAC value greater than about 250 ORAC units per 30 ml of product.

10. The dietary supplement of claim 9, wherein the fruit concentrate comprises one or more fruits selected from the group consisting of raspberries, blueberries, grapes, blackberries, strawberries, plums, oranges, cherries, and kiwi fruits, currants, elderberries, black currants, and cranberries.

11. The dietary supplement of claim 6, further comprising at least one sweetener composition selected from the group consisting of lemon juice flavoring, stevia, agave nectar, sucralose, and corn syrup.

12. The dietary supplement of claim 6, wherein the dietary supplement has a pH from about 3 to about 4.

* * * * *